United States Patent [19]

Mendelson et al.

[11] Patent Number: 5,372,135
[45] Date of Patent: Dec. 13, 1994

[54] BLOOD CONSTITUENT DETERMINATION BASED ON DIFFERENTIAL SPECTRAL ANALYSIS

[75] Inventors: Yitzhak Mendelson, Worcester; Hannu Harjunmaa, Holden; Yi Wang; Brian D. Gross, both of Worcester, all of Mass.

[73] Assignee: VivaScan Corporation, Worcester, Mass.

[21] Appl. No.: 216,083

[22] Filed: Mar. 21, 1994

Related U.S. Application Data

[63] Continuation of Ser. No. 815,469, Dec. 31, 1991, abandoned.

[51] Int. Cl.$^5$ .................................................. A61B 5/00
[52] U.S. Cl. .................................... 128/633; 128/666; 356/39
[58] Field of Search .................... 128/633–634, 128/664–666; 356/39–41; 422/82.09

[56] References Cited

U.S. PATENT DOCUMENTS

| | | |
|---|---|---|
| 1,758,088 | 5/1930 | Schmick . |
| 2,721,942 | 10/1955 | Friel et al. ............................ 250/435 |
| 3,463,142 | 8/1969 | Harte ...................................... 128/633 |
| 3,614,450 | 10/1971 | Hill et al. .............................. 250/210 |
| 3,638,640 | 2/1972 | Shaw ..................................... 356/41 |
| 3,926,527 | 12/1975 | Pembrook et al. ..................... 356/246 |
| 3,958,560 | 5/1976 | March ................................... 356/39 |
| 3,963,019 | 6/1976 | Quandt .................................. 356/39 |
| 4,029,085 | 6/1977 | Dewitt et al. ......................... 128/2 R |
| 4,033,330 | 7/1977 | Willis et al. .......................... 356/39 |
| 4,169,676 | 10/1979 | Kaiser ................................... 128/633 |
| 4,266,554 | 5/1981 | Hamaguri .............................. 128/633 |
| 4,267,844 | 5/1981 | Yamanishi ............................. 128/633 |
| 4,306,877 | 12/1981 | Lubbers ................................. 23/230 R |
| 4,321,930 | 3/1982 | Jobsis et al. .......................... 128/633 |
| 4,380,240 | 4/1983 | Jobsis et al. .......................... 128/633 |
| 4,398,541 | 8/1983 | Pugliese ................................ 128/665 |
| 4,427,889 | 1/1984 | Muller ................................... 250/339 |
| 4,485,820 | 12/1984 | Flower .................................. 128/633 |
| 4,490,845 | 12/1984 | Steinbruegge et al. .............. 250/210 |
| 4,513,751 | 4/1985 | Abe et al. .............................. 128/2 R |
| 4,523,279 | 6/1985 | Sperinde et al. . |
| 4,570,638 | 2/1986 | Stoddart et al. ...................... 128/665 |
| 4,586,513 | 5/1986 | Hamagur .............................. 125/633 |
| 4,603,700 | 8/1986 | Nichols et al. ........................ 128/633 |
| 4,621,643 | 11/1986 | New, Jr. et al. ....................... 128/633 |
| 4,653,498 | 3/1987 | New, Jr. et al. ....................... 128/633 |
| 4,655,225 | 4/1987 | Dahne et al. .......................... 128/633 |
| 4,704,029 | 11/1987 | Van Heuvelan ....................... 356/39 |
| 4,725,147 | 2/1988 | Stoddart ................................ 356/433 |
| 4,750,496 | 6/1988 | Reinhart et al. ...................... 128/635 |
| 4,759,369 | 7/1988 | Taylor ................................... 128/633 |
| 4,768,516 | 9/1988 | Stoddart et al. ...................... 128/665 |
| 4,785,814 | 11/1988 | Kane . |
| 4,796,636 | 1/1989 | Branstetter et al. .................. 128/33 |

(List continued on next page.)

FOREIGN PATENT DOCUMENTS

| | | |
|---|---|---|
| 0404562A3 | 12/2790 | . |
| 0074428 | 3/1983 | Germany . |
| 0407992 | 1/1991 | Japan . |
| 0152979 | 8/1985 | Netherlands . |
| 0160768 | 4/1984 | Switzerland . |
| PCT/US90/-00394 | 1/1990 | WIPO . |

OTHER PUBLICATIONS

R. A. Peura and Y. Mendelson, "Blood Glucose Sensors: An Overview" IEEE/NSF Symposium on Biosensors, pp. 63–68 (1984).

Donahoe and Longini, "A New Noninvasive Backscattering Oximeter," Proc. IEEE/Seventh Annual Conf.
(List continued on next page.)

Primary Examiner—Angela D. Sykes
Attorney, Agent, or Firm—Hamilton, Brook, Smith & Reynolds

[57] ABSTRACT

The present invention relates to the determination of an analyte or multiple analytes in blood using information derived from the differential optical absorption spectra of blood. Specifically, the information is derived from the differential spectra of tissue before and immediately after the volume of blood in the tissue has been changed.

16 Claims, 4 Drawing Sheets

U.S. PATENT DOCUMENTS

| | | | |
|---|---|---|---|
| 4,805,623 | 2/1989 | Jobsis | 128/633 |
| 4,817,623 | 4/1989 | Stoddart et al. | 128/665 |
| 4,832,484 | 5/1989 | Aoyagi et al. | 356/41 |
| 4,854,699 | 8/1989 | Edgar, Jr. . | |
| 4,863,265 | 9/1989 | Flower et al. | 356/41 |
| 4,867,557 | 9/1989 | Takatani et al. . | |
| 4,882,492 | 11/1989 | Schlager | 250/346 |
| 4,883,055 | 11/1989 | Merrick | 128/633 |
| 4,927,264 | 5/1990 | Shiga et al. | 356/41 |
| 4,975,581 | 12/1990 | Robinson et al. | 250/339 |
| 5,028,787 | 7/1991 | Rosenthal et al. | 250/341 |
| 5,054,487 | 10/1991 | Clarke . | |
| 5,178,142 | 1/1991 | Harjunmaa et al. | 128/633 |
| 07/511,229 | 4/1991 | Mendelson et al. | 128/633 |
| 07/511,341 | 4/1991 | Harjunmaa et al. | 356/39 |
| 07/527,514 | 5/1990 | Harjunmaa et al. | 250/345 |
| 07/725,441 | 7/1991 | Harjunmaa et al. . | |
| 07/725,502 | 7/1991 | Harjunmaa et al. . | |
| 07/806,144 | 12/1991 | Mendelson . | |

OTHER PUBLICATIONS

*Eng. in Medicine and Biology Society*, pp. 144–147 (1985).

H. M. Heise and R. Marcbach, "Multivariate Determination of Glucose in Whole Blood by Attenuated Total Reflection Infrared Spectroscopy", *Analytical Chemistry*, 61(18):2009–2015 (1989).

M. A. Arnold and G. W. Small, "Determination of Physiological Levels of Glucose in an Aqueous Matrix with Digitally Filtered Fourier Transform Near–Infrared Spectra.", *Anal. Chem*, 62:1457–1464, (1990).

R. Marbach and H. M. Heise, "Calibration Modeling by Partial Least–Squares and Principal Component Regression and its Optimization Using an Improved Leverage Correction for Prediction Chemometrics and Intelligent Laboratory Systems" 9:45–63 (1990).

P. A. Jansson, *Neural–Networks: An Overview, Analytical Chemistry*, vol. 63, No. 6, pp. 357A–362A, (1991).

BLOOD CONSTITUENT DETERMINATION BASED ON DIFFERENTIAL SPECTRAL ANALYSIS

RELATED APPLICATION

This application is a continuation of co-pending application Ser. No. 07/815,469 filed Dec. 31, 1991, now abandoned.

RELATED APPLICATIONS

The following are related applications: U.S. Ser. No. 07/511,341 filed Apr. 4, 1990, now U.S. Pat. No. 5,112,124, entitled "Method and Apparatus for Measuring the Concentration of Absorbing Substances"; U.S. Ser. No. 07/511,229 filed Apr. 19, 1990, now U.S. Pat. No. 5,137,023 entitled "Method and Apparatus for Monitoring Blood Analytes Noninvasively by Pulsatile Photoplethysmography"; U.S. Ser. No. 07/527,514 filed May. 23, 1990, now U.S. Pat. No. 5,099,123 entitled "Method for Determining by Absorption of Radiations the Concentration of Substances in Absorbing and Turbid Matrices"; U.S. Ser. No. 07/725,502 filed Jul. 3, 1991, now U.S. Pat. No. 5,183,042 entitled "Electromagnetic Method and Apparatus to Measure Constituents of Human or Animal Tissue" and U.S. Ser. No. 07/725,441 filed Jul. 3, 1991, now U.S. Pat. No. 5,178,142 entitled "Electromagnetic Method and Apparatus to Measure Constituents of Human or Animal Tissue", each of which is incorporated by reference herein.

FIELD OF THE INVENTION

This invention relates to instrumentation and methods for noninvasive quantitative measurement of biochemical blood constituents such as blood glucose, urea, cholesterol, etc.

BACKGROUND OF THE INVENTION

The determination of blood glucose is critical to diabetic patients. These patients must measure their blood glucose level several times daily in order to determine how much insulin their body requires. For diabetics with internally implantable or external insulin pumps, the ability to have a reliable glucose sensor that can continuously measure their blood glucose is essential for the realization of an artificial pancreas device.

Considerable efforts have been placed on the development of reliable methods for measuring blood glucose noninvasively. Although several sensors have been successfully developed for in vitro and in vivo applications, these sensors can be used only for intermittent measurements or short term monitoring. None of these devices are suitable for long-term in vivo applications utilizing noninvasive means.

The concentration of a limited number of analytes in blood can be measured noninvasively by spectroscopic means. For instance, by measuring the amount of optical radiation either absorbed by, transmitted through or reflected from biological tissues, it is possible to derive a quantitative measurement relative to the concentration of oxygen in blood. In contrast to invasive measurement, noninvasive measurements are clearly more attractive because they are safe, fast, convenient, painless and can be used to provide short-term and long-term continuous information on changing levels of blood analytes in the body. Therefore, noninvasive measurement of blood constituents is desirable, especially in children and older patients.

Several attempts have been made in the past to develop a reliable method for quantitative noninvasive measurement of glucose levels in biological tissues by irradiating the tissue with light at predetermined wavelengths and using the principle of absorption spectroscopy. Some methods are based on detecting the resonance absorption peaks in the infrared region of the electromagnetic spectrum, also known as the "fingerprints" region, which are caused by vibrational and rotational oscillations of the molecules and are characteristic for different molecules. Other techniques are based upon near-infrared spectroscopy to determine the sample's composition. Unlike the "fingerprint" region, which is valuable as a tool for obtaining structural information on the sample, structural measurements in the near infrared region of the spectra are obscured because of multiple and weak overtones yielding many overlapping peaks.

Regardless of which spectroscopic method is employed, there are four basic practical difficulties which limit the noninvasive detection of most biological substances including glucose: 1) The high intrinsic background absorption by water, 2) the relatively low concentration of most biological substances, 3) the number of weak and overlapping absorption peaks in the spectra, and 4) the highly scattering properties of biological tissues. Moreover, the large variations in the optical properties of skin among different individuals makes absolute measurements and calibrations very difficult and impractical.

Two methods are commonly utilized for obtaining spectral information from biological tissues for the purpose of measuring the concentration of various biochemical constituents noninvasively. One method is based on information derived from the absolute optical spectra of tissues containing blood. According to this concept, the tissue is illuminated with light at different preselected wavelengths and either the total or proportional amount of light which is transmitted through, reflected from, or transflected by the tissue is measured by a photodetector. This technique was utilized for example by Hewlett-Packard in their ear oximeter product (U.S. Pat. No. 3,638,640 by Shaw) and by Rosenthal et al. (U.S. Pat. No. 5,028,787). According to the other method, which is widely used in pulse oximetry, the tissue is illuminated by two different light sources. Typically, one wavelength around 660 nm and the other in the range between 815 nm and 960 nm are used. The change in optical absorption caused by the pulsation of arterial blood in the tissue is measured and analyzed to provide a quantitative measure of the amount of oxygen present in the arterial blood. According to this second technique, the ratio between the normalized pulsatile and nonpulsatile components of a single pair of red and infrared wavelengths transmitted through tissue is used to compute the amount of oxygen saturation in the arterial blood. Both of these methods are useful for measuring, for example, the oxygen saturation in blood but cannot be readily utilized for measuring the concentration of glucose or other low concentration substances in blood. The reasons are related to the fact that the optical absorption spectra of oxyhemoglobin, which corresponds to fully oxygenated blood, and deoxyhemoglobin, which corresponds to fully deoxygenated blood, are significantly different from each other. Furthermore, the optical absorption spectra of blood in the 660 to 9660 nm region of the spectrum is significantly stronger than the background optical absorption of the blood-less tissue. Lastly, the relative concentration of hemoglobin is normally about 150 times higher than that of glucose and hemoglobin has a much higher optical absorption compared to that of glucose.

SUMMARY OF THE INVENTION

The present invention is based on information derived from the continuous differential spectra of blood obtained noninvasively through the skin by illuminating the tissue with light which rapidly varies in frequency over time. This differential optical spectra (absorption vs. wavelength) is obtained by measuring the difference between the total attenuation of tissue containing a first volume of blood and the same tissue containing a second volume of blood, which is an incremental or a decremental change from the first volume of the blood. Information related to the content of glucose in the blood is then derived from analyzing the features of this differential spectra over a selected range of wavelengths.

DETAILED DESCRIPTION OF THE DRAWINGS

Figure 1:
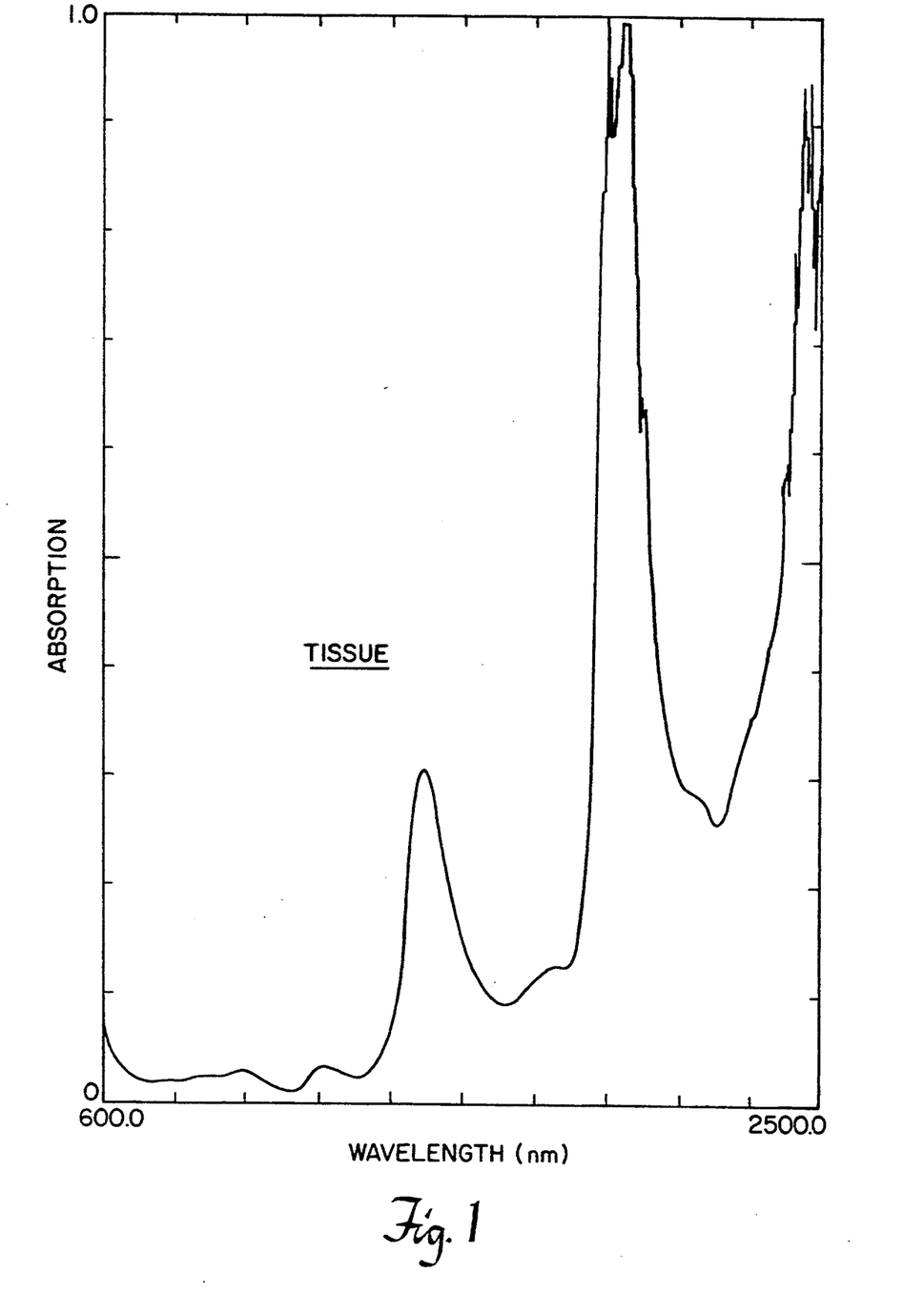
FIG. 1 is a normalized plot of a typical optical spectrum (absorption vs. wavelength) of tissue containing blood.
Figure 2:
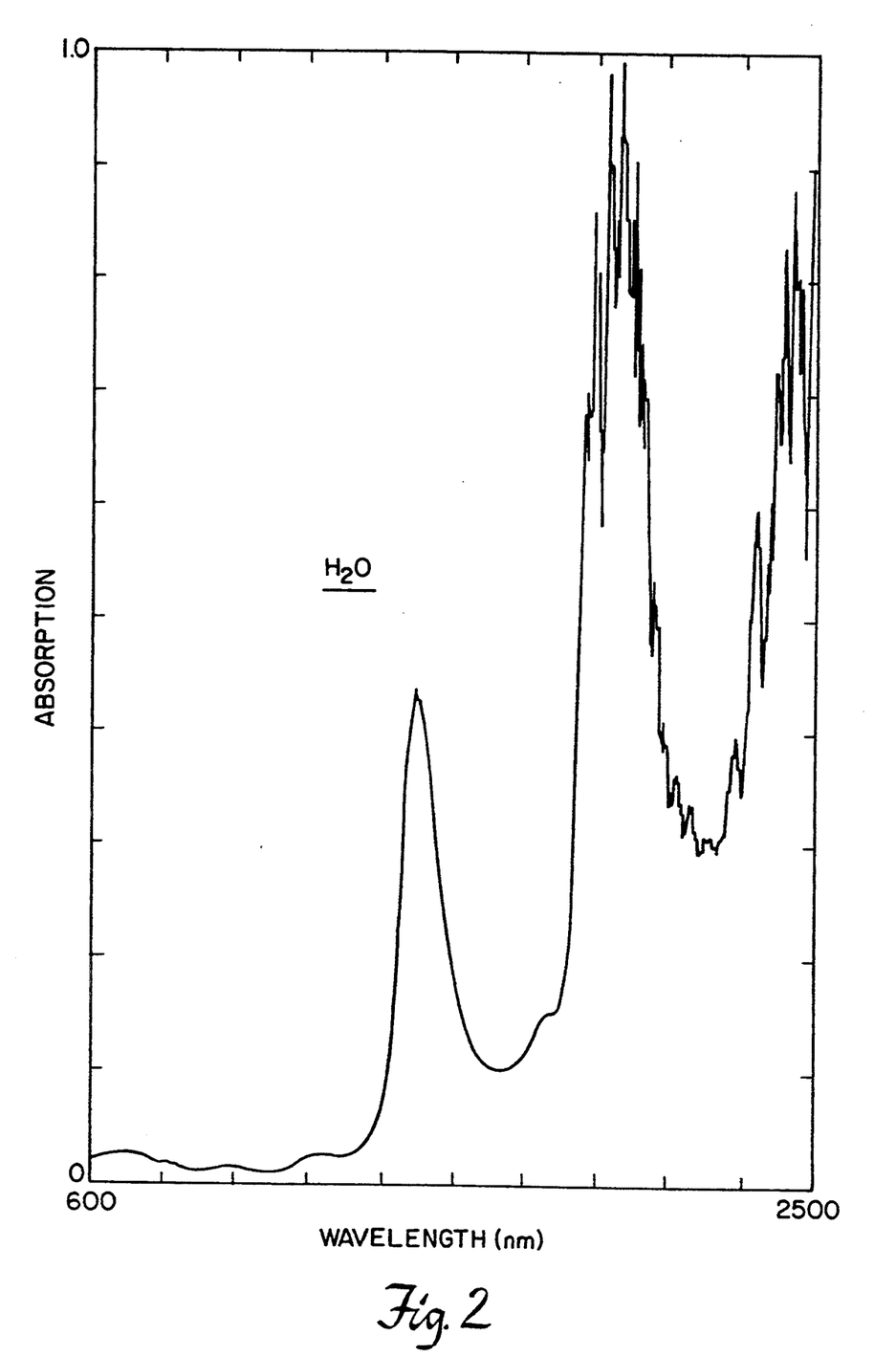
FIG. 2 is a normalized plot of a optical absorption spectrum of water.

The spectrum shown in FIG. 1 represents a typical optical transmission spectrum of tissue containing blood acquired by a spectrophotometer in the wavelength region between 600 nm in the visible and 2500 nm in the infrared. The basic shape and relative magnitude of the absorption peaks in this spectra are similar to that of water (as shown for comparison in FIG. 2) which is known to be the major optical interfering constituent in blood and tissues for in vivo infrared spectroscopy. If the concentration of glucose in the blood is changed within physiological ranges compatible with life, the basic features of the spectra shown in FIG. 1 will remain unchanged, namely, the difference between the two spectra is so minute that it cannot be detected with ordinary spectrophotometers equipped with photodetectors sensitive to radiation in the corresponding infrared region. The main reason for that is the intrinsically high optical absorption of water compared to glucose and the relatively smaller concentration of glucose compared to that of water in blood and living tissue. In practical terms, in order to be able to detect variations in the optical absorption spectra of living tissue as a result of changes in the concentration of glucose in that tissue, it is essential to use an optical detector which can discriminate between changes in light intensities amounting to levels well below the intrinsic noise level of the optical detector itself. With the present state of the technology, this is impractical to accomplish. The present invention overcomes this problem by generating a differential spectrum which contains information that is significantly more sensitive to physiological variations in the level of blood glucose.

Figure 3:
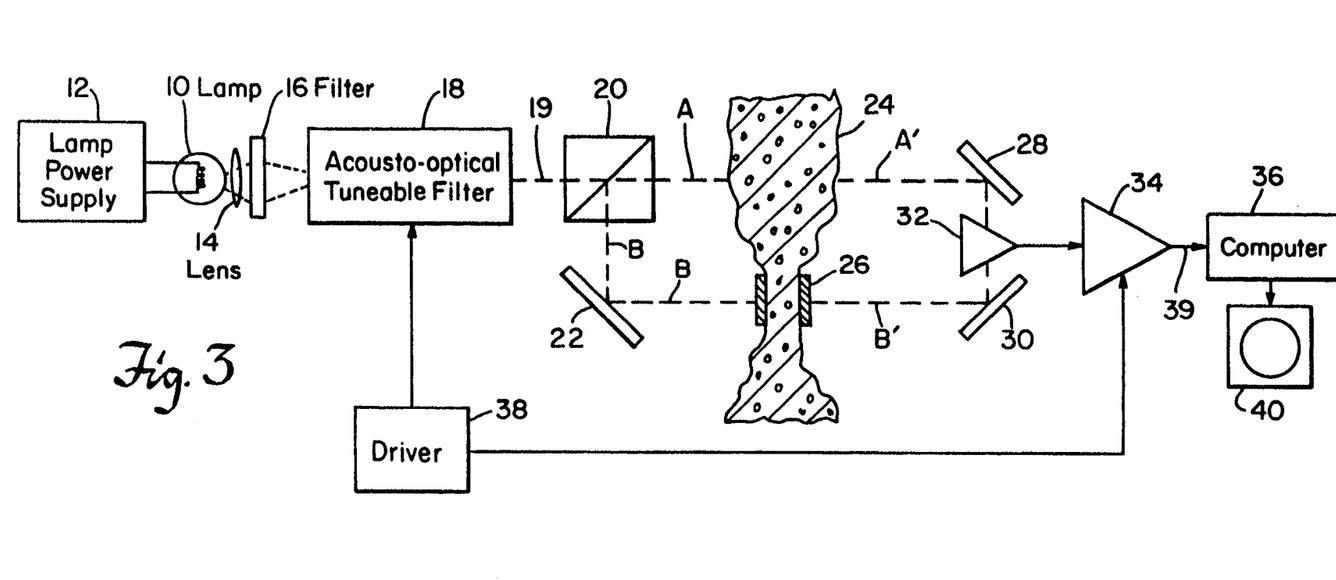
FIG. 3 is a block diagram of an apparatus for determining blood analyte concentration in vivo using differential spectrum analysis.

FIG. 3 illustrates how this differential spectra is generated. A light source 10, for example a quartz halogen lamp, powered by a power supply 12 is used to generate light in the wavelength region of interest. The light generated by the lamp is focused by optical lenses 14 onto optically tuneable filter 18. Alternatively, a narrow range of wavelengths can be pre-selected by passing the beam through an appropriate optical filter 16. The variable optical filter 18 is powered by an electronic driver 38. Filter 18 is used to select a certain wavelength and intensity beam of light 19 at its output. Preferably filter 18 comprises an acousto-optical tuneable filter (AOTF) which is a solid-state tuneable bandpass optical filter that allows very fast (fractions of a second, or less) narrow wavelength scanning. Other means of generating a fast scanning monochromatic light beam can also be used, instead.

The light 19 is divided by beam splitter 20 into two beams A and B. Beam B is reflected by mirror 22 and enters body tissue 24 at a site adjacent to the entry point of beam A.

The blood volume at the site of entry of beam A is greater than at entry of beam B. Modulation of the blood volume at the adjacent sites may be accomplished in a number of ways. In FIG. 3 a suitable tissue site such as an ear lobe or hand web is used and a light transparent clamp 26 is applied to the entry site of beam B to compress the tissue at that location. Similar light beams A and B enter the tissue 24 and after being partially absorbed by the tissue emerge as light beams A' and B'. Beams A' and B' are reflected by mirrors 28 and 30 onto a single photodetector and preamplifier 32 to produce an electrical signal corresponding to the differential spectra of the two adjacent tissue sites; therefore representing the differential absorptive spectra of blood.

Figure 4A:
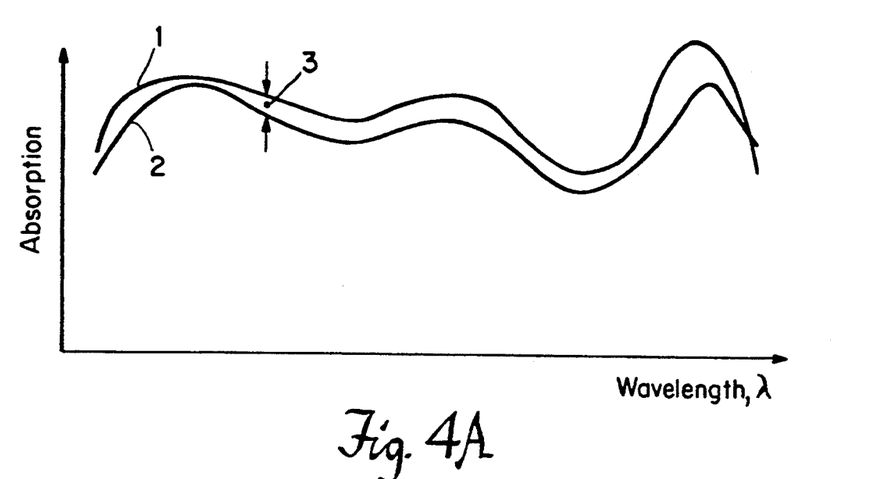
FIG. 4A are two optical absorption spectra of tissue taken from the same tissue site for two different volumes of blood.
Figure 4B:
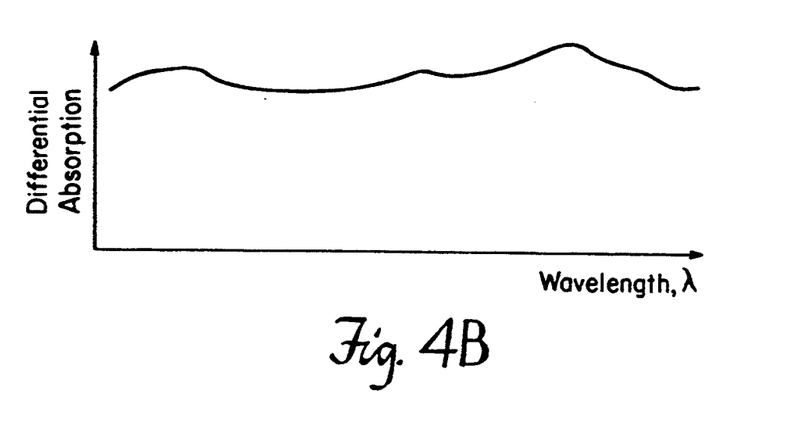
FIG. 4B is a normalized differential optical absorption spectrum corresponding to the spectra shown in FIG. 4A.

This differential spectra is illustrated in FIG. 4B which shows the results of subtracting the absorptive spectra of beam A passing through the site with greater blood volume (Curve A of FIG. 4A) with the absorptive spectra of beam B passing through the lesser volume site (Curve B of FIG. 4A).

The driver 38 consists of a high frequency oscillator and power amplifier and is also used to chop the light propagating though the tuneable filter such that the output 19 is a train of optical pulses with a predetermined duty cycle, frequency, wavelength and intensity. The output of the photodetector/preamplifier 32 is further amplified by a sensitive amplifier 34 which can be a lock-in amplifier. If a lock-in amplifier is used, a reference signal taken from the driver 38 is used to synchronize the AOTF (18) with the lock-in amplifier. The output from this amplifier 39 is acquired by a computer 36 which is used to process the data and derive the information related to the concentration of the unknown analyte for presentation by a read-out meter 40.

The spectra shown in FIG. 4B represent the differential spectra of tissue generated by modulating the amount of blood in the tissue. Therefore, the shape of this spectra is characteristic of the spectra of blood.

Since blood contains many biochemical analytes in addition to glucose, the spectra shown in FIG. 4B is a composite broad spectra and it contains information relative to the concentration of many blood analytes, including glucose. Some wavelength ranges (for example, 1580 to 1640 nm) contain information predominantly characteristic of blood glucose whereas other wavelengths (for example 1700–1750 nm) convey information predominantly related to other blood analytes, such as lipids. In order to derive information on blood glucose concentration, the spectra in FIG. 4B must be processed in a computer 36 using a number of different mathematical algorithms utilizing, for example, various known multivariate calibration techniques (see, for example, the book by H. Martens and T. Naes entitled "Multivariate Calibration", published by John Wiley and Sons, New York, 1989) such as: Partial Least-Squares (e.g., see paper by H. Michael Heise, Ralf Marbach, et al., "Multivariate Determination of Glucose in Whole Blood by Attenuated Total Reflection Infrared Spectroscopy" in *Analytical Chemistry*, Vol. 61, No. 18, Sep. 15, pp. 2009–2015, 1989), Principal Component Regression (e.g., see paper by R Marbach and H. M. Heise, "Calibration Modeling by Partial Least-Squares and Principal Component Regression and its Optimization Using an Improved Leverage Correction for Prediction Testing" in *Chemometrics and Intelligent Laboratory Systems*, Vol. 9, pp. 45–63, 1990), special Fourier filtering procedures (e.g., see paper by Mark A. Arnold and Gary W Small, "Determination of Physiological Levels of Glucose in an Aqueous Matrix with Digitally Filtered Fourier Transform Near-Infrared Spectra", *Analytical Chemistry*, Vol. 62, pp. 1456–1464, 1990), neural networks (e.g., see paper by Peter A. Jansson, "Neural Networks: An Overview" in *Analytical Chemistry*, Vol. 63, No. 6, March 15, pp. 357A–362A, 1991), etc. The resultant determination may then be presented in various forms on display 40.

The optical detection system described above has the ability to instantaneously frequency scan a tissue containing two different blood volumes such that the physiological and biochemical variables in the tissue remain virtually the same between consecutive scans. Conventional optical scanning devices, such as diffracting gratings or a mechanical device which consists of multiple band-pass interference filters mounted perpendicular to the incident light beam or tilted at different angles with respect to the incident beams, are not suitable for this application because they are too slow and the poor wavelength reproducibility of these mechanical devices is a major limiting factor when trying to measure small changes in the optical absorption spectra of the tissue. The unique properties of the electronic AOTF are utilized in this invention to generate a differential spectra from a living tissue which is similar to the intrinsic optical absorption property of blood.

Figure 5:
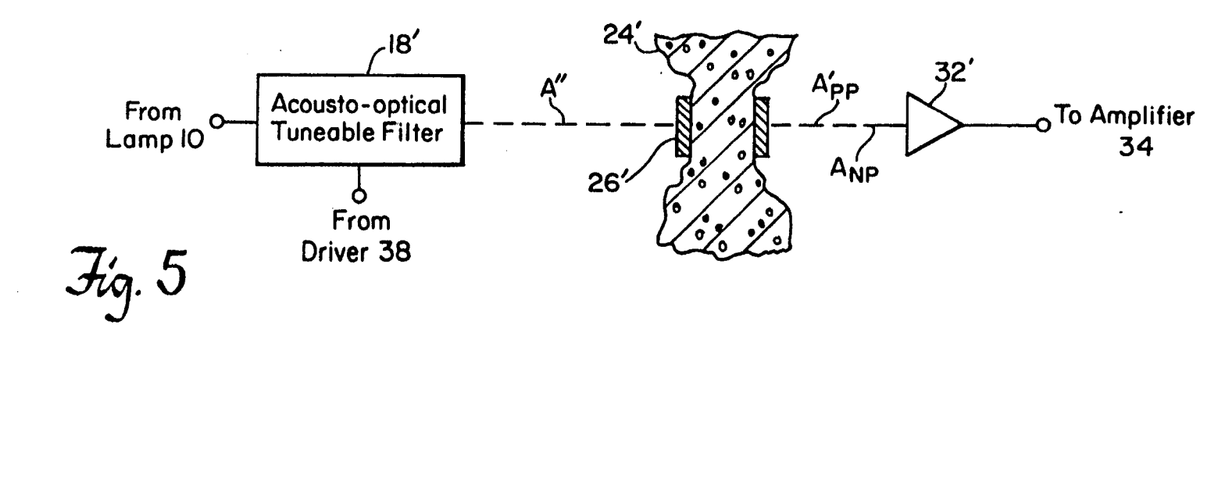
FIG. 5 is a block diagram showing an alternate embodiment of FIG. 3.

Another embodiment of this invention is shown in FIG. 5. According to this arrangement, a single tissue site 24' is illuminated by a single beam A" generated, for example, by an AOTF device 18'. The blood content in this tissue is changed by rapidly applying an external pressure on the tissue using for instance a light transparent electro-mechanically squeezing head or clamp 26'. The properties of this head is such that it allows light to be transmitted through the tissue and it can be used to change the thickness of the tissue simultaneously during the measurement. Since the AOTF is capable of switching wavelengths at extremely high rates, it is possible to apply a quick external pressure pulse to squeeze out some of the blood in the tissue without causing any damage to the tissue or without altering the biochemical status of the tissue and take two successive scans of the tissue. One scan $A_{NP}$ is obtained before the external pressure pulse is applied to the tissue and the second scan $A_{pp}$ is obtained immediately after the external pressure pulse is applied. The two scans are then subtracted from each other in detector/preamplifier unit 32' to provide the differential spectra, which is further amplified by amplifier 34, as shown in FIG. 3. This procedure can be repeated several times in a periodic manner in order to acquire multiple scans which can then be averaged in time to improve the overall signal-to-noise ratio of the measurement.

Figure 6:
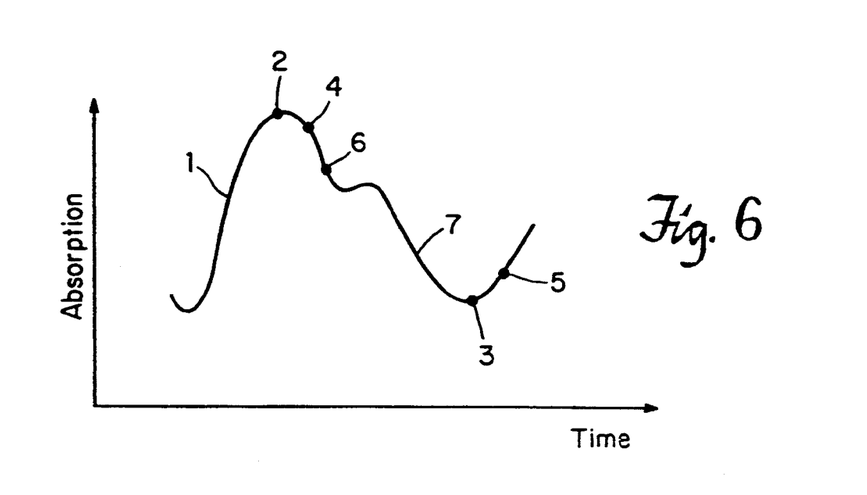
FIG. 6 is a plot of tissue absorption versus time during the normal cardiac cycle.

Alternatively, as shown in the typical photoplethysmogram of FIG. 6, the same procedure can be utilized without the external application of pressure by relying on the presence of the natural blood pressure pulse 1 to modulate the amount of blood in the tissue. The block diagram shown in FIG. 5 is suitable for performing this measurement, except that the electro-mechanically squeezing clamp 26' is not required. Accordingly, a fast wavelength scan between 1100 nm and 2500 nm is first obtained during the peak systolic phase of the blood pressure pulse point #2 and then the same wavelength scan is repeated during the peak diastolic period of the blood pressure point #3, as illustrated in FIG. 6. These two scans do not need to be synchronized with the peak and valley of the blood pressure waveform 1 but can occur at different times in the cardiac cycle, for example, points 4 and 5, or points 6 and 7, provided the two consecutive wavelength scans occur when different amounts of blood are present inside the tissue.

As shown in FIG. 6, a separate absorption versus time spectrum is generated each time there is a change in the volume of blood in the tissue. The difference between these spectra will have features similar to that depicted in FIG. 4B. Absolute calibration of the measurement is obtained by numerically correlating the features of this differential absorption spectra, shown, for example, in FIG. 4B with different concentrations of glucose during an empirical calibration study in patients or volunteers undergoing standard glucose tolerance tests. These spectral features consist of local peaks and valleys corresponding to regions in the spectra where various blood analytes absorb the optical radiation by different amounts.

The present invention overcomes the deficiencies in the prior art in several ways. Firstly, it provides a simple way to obtain absolute spectral data from blood by eliminated or canceling out the major optical interference caused by the skin and other non-blood components in the tissues. This makes the measurement significantly more accurate and repeatable since the optical properties of blood are similar among different individuals whereas the optical properties of skin and bloodless tissues are unpredictable and can vary widely among different subjects. Secondly, it allows significantly higher measurement sensitivity for physiological variations in the concentration of glucose and other analytes in blood. Thirdly, it provides a method for absolute calibration of the measurement.

Although the method described in this invention relates to the measurement of glucose in blood, it should be understood that the same technique is also applicable for measurement of other low concentration biochemical analytes in blood such a urea, alcohol, cholesterol, and various other important blood constituents of clinical relevance.

Equivalents

Those skilled in the art will recognize, or be able to ascertain, using no more than routine experimentation, many equivalents to the specific embodiments of the invention described herein.

For example, while the invention is illustrated by a transmission of light through tissue, reflected light, raman spectroscopy, fluorescence, or any other optical technique may also be utilized in a similar manner.

We claim:

1. A non-invasive in vivo method for obtaining a differential absorption spectrum relating to the concentration of analyte in living tissue comprising the steps of:
   a) illuminating the tissue with a first light beam which is varied in wavelength in a substantially continuous manner about a first wavelength over a first time period;
   b) detecting the wavelength varied first light beam after the beam has traversed a first blood volume of tissue containing said analyte to produce a first absorption spectrum comprising a substantially continuous plot of absorption in said first volume versus wavelength;
   c) changing the blood volume of tissue;
   d) illuminating the changed blood volume of tissue with a second light beam which is varied in wavelength in a substantially continuous manner about a second wavelength over a second time period;
   e) detecting the wavelength varied second light beam after the beam has traversed a second blood volume of tissue containing said analyte to produce a second absorption spectrum comprising a substantially continuous plot of absorption in said changed volume versus wavelength;
   f) combining the two absorption spectrums to produce a differential absorption spectrum.

2. The method of claim 1 including processing of the differential spectrum to determine analyte concentration.

3. The method of claim 2 wherein the analyte is glucose.

4. The method of claim 2 including detecting of the light by a photodetector and wherein the absorption spectrum is comprised of an electrical signal.

5. The method of claim 1 including varying the wavelength of at least one of said first and second light beams over a range between about 1100 nanometers and 2500 nanometers.

6. The method of claim 1 wherein the blood volume is changed electromechanically.

7. The method of claim 1 wherein the blood volume is changed by the natural blood pressure pulse of the cardiac cycle.

8. The method of claim 1 wherein the wavelength is varied in step d) over a range which is similar to the wavelength variation in step a).

9. A non-invasive method for obtaining a differential absorption spectrum relating to the concentration of analyte in living tissue comprising the steps of:
   a) illuminating the tissue at a first tissue site with a light beam which is varied in wavelength during a first time period;
   b) during a second time period changing the blood volume of the tissue at the first tissue site from a first volume to a second volume;
   c) detecting the light beam during the first time period after the wavelength varied beam has traversed the first volume of tissue containing said analyte to produce a first absorption spectrum;
   d) detecting the light beam during the second time period after the wavelength varied beam has traversed the second volume of tissue containing said analyte to produce a second absorption spectrum;
   e) combining the two absorption spectrum to produce a differential absorption spectrum which represents tissue absorption versus a spectrum of wavelengths.

10. The method of claim 9 including processing the differential spectrum to determine analyte concentration.

11. The method of claim 9 wherein the analyte is glucose.

12. Apparatus for non-invasive generation of a differential signal relating to the concentration of analyte in living tissue comprising:
   a) a light source generating a beam of light;
   b) a tuner varying the frequency of said beam of light over a predetermined time period;
   c) a photosensitive detector for detecting said frequency varying light after traversing said tissue:
      (ii) when the tissue contains a first volume of blood; and
      (iii) when the tissue contains a second volume of blood; to produce two separate absorption signals a first one of which is proportional to the absorption of said frequency varying light by said tissue containing the first volume of blood versus frequency and a second of which is proportional to the absorption of said frequency varying light by said tissue containing the second volume of blood versus frequency; and
   d) generating means for generating said differential signal which is proportional to the difference between the light detected versus frequency for each signal detected in (c) (i) and (ii) above.

13. The apparatus of claim 12 wherein the tuner comprises an acousto-optical tunable filter.

14. The apparatus of claim 12 including a beam splitter dividing the frequency varied beam of light into two beams, one of which traverses a greater volume of blood than the other.

15. The apparatus of claim 12 including clamp means for varying the volume of blood in the tissue traversed by the light.

16. The apparatus of claim 15 wherein the clamp means is an optically transparent body.

* * * * *

UNITED STATES PATENT AND TRADEMARK OFFICE
CERTIFICATE OF CORRECTION

PATENT NO. : 5,372,135
DATED : Dec. 13, 1994
INVENTOR(S) : Yitzhak Mendelson, Hannu Harjunmaa, Yi Wang and Brian D. Gross It is certified that error appears in the above-indentified patent and that said Letters Patent is hereby corrected as shown below:

Col. 7, line 56, delete "wherein" and insert --including changing--.

Col. 7, line 57, delete "is changed".

Col. 8, line 33, after "detector" delete --for--.

Col. 8, line 35, delete "(ii)" and insert --(i)--.

Col. 8, line 37, delete "(iii)" and insert --(ii)--.

Signed and Sealed this

Eleventh Day of April, 1995

Attest:

BRUCE LEHMAN

Attesting Officer     Commissioner of Patents and Trademarks